United States Patent [19]

Smith

[11] Patent Number: 5,374,251

[45] Date of Patent: Dec. 20, 1994

[54] MEDICAL FLUID PUMP APPARATUS

[75] Inventor: Larry C. Smith, Shawnee, Kans.

[73] Assignee: Entracare, Lenexa, Kans.

[21] Appl. No.: 46,620

[22] Filed: Apr. 14, 1993

[51] Int. Cl.$^5$ ............................................. A61M 1/00
[52] U.S. Cl. .................................. 604/151; 604/67; 604/153; 417/477.12
[58] Field of Search ................. 604/67, 131, 151, 153, 604/251, 253; 128/DIG. 13; 417/474–477

[56] References Cited

U.S. PATENT DOCUMENTS

| | | |
|---|---|---|
| 3,740,173 | 6/1973 | Natelson . |
| 4,080,967 | 3/1978 | O'Leary . |
| 4,137,913 | 2/1979 | Georgi . |
| 4,184,815 | 1/1980 | Casson et al. . |
| 4,187,057 | 2/1980 | Xanthopoulos . |
| 4,210,138 | 7/1980 | Jess et al. . |
| 4,221,543 | 9/1980 | Cosentino et al. . |
| 4,236,880 | 12/1980 | Archibald ............ 604/153 |
| 4,278,085 | 7/1981 | Shim . |
| 4,312,341 | 1/1982 | Zissimopoulos et al. . |
| 4,363,609 | 12/1982 | Cosentino et al. . |
| 4,460,358 | 7/1984 | Somerville et al. . |
| 4,496,295 | 1/1985 | King ........................ 417/477 |
| 4,515,535 | 5/1985 | D'Silva ..................... 604/153 |
| 4,557,725 | 12/1985 | Heyne et al. . |
| 4,568,254 | 2/1986 | Terada et al. . |
| 4,585,399 | 4/1986 | Baier . |
| 4,585,441 | 4/1986 | Archibald . |
| 4,631,007 | 12/1986 | Olson ....................... 604/153 |
| 4,650,469 | 3/1987 | Berg et al. . |
| 4,652,260 | 3/1987 | Fenton, Jr. et al. . |
| 4,673,389 | 6/1987 | Archibald et al. . |
| 4,714,463 | 12/1987 | Archibald et al. . |
| 4,798,590 | 1/1989 | O'Leary et al. . |
| 4,913,703 | 4/1990 | Pasqualucci et al. ....... 604/151 |
| 4,976,590 | 12/1990 | Baldwin .................... 417/477 |
| 5,127,908 | 7/1992 | Walker et al. ............ 604/153 |
| 5,147,313 | 9/1992 | Dikeman .................... 604/153 |
| 5,151,019 | 9/1992 | Danby et al. .............. 417/474 |

*Primary Examiner*—John D. Yasko
*Assistant Examiner*—Anthony Gutowski
*Attorney, Agent, or Firm*—Hovey, Williams, Timmons & Collins

[57] ABSTRACT

A medical fluid pump apparatus is provided for use with a fluid delivery set including a fluid reservoir, a delivery outlet, and tubing connecting the reservoir to the outlet. The apparatus includes a pump supported on a housing, and a shelf spaced from the pump and provided with a pair of spaced, transverse slots sized for receipt of the tubing of the fluid delivery set so that the tubing of the fluid delivery set may be received in the slots and placed in operative engagement with the peristaltic pump. A latch is supported on the housing for movement between a closed position in which the latch blocks the slots to prevent the removal of the tubing and an open position in which the latch exposes the slots.

18 Claims, 2 Drawing Sheets

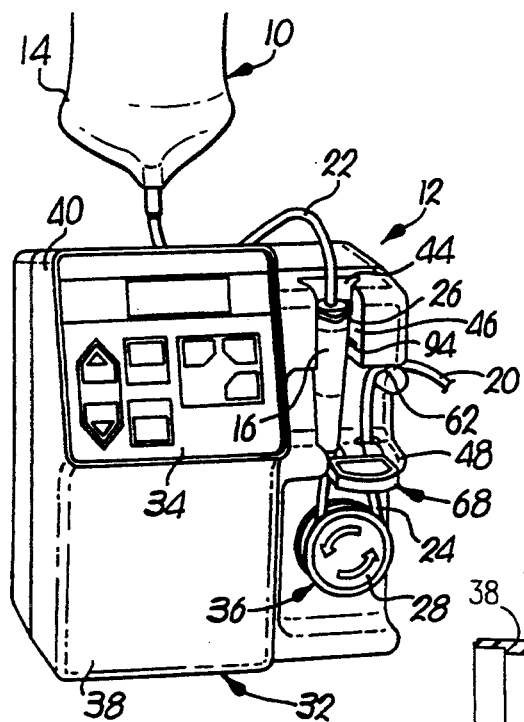
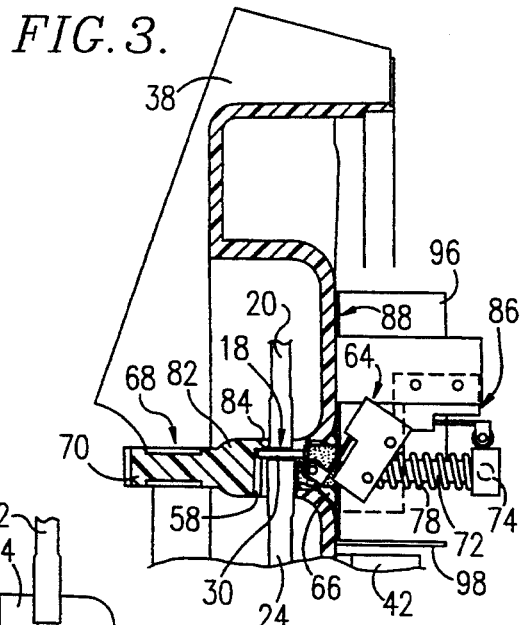
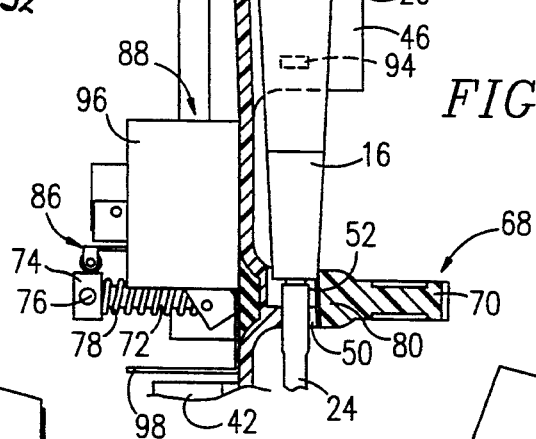
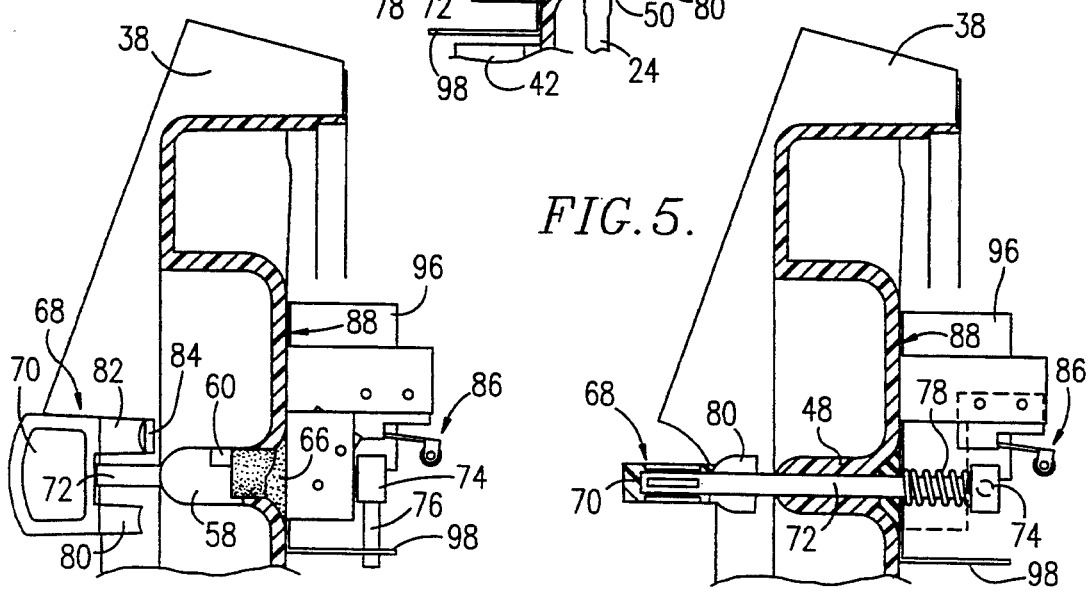

MEDICAL FLUID PUMP APPARATUS

BACKGROUND OF THE INVENTION

1. Field of the Invention

The present invention relates generally to medical fluid pumping devices and, more particularly, to a pump apparatus having a latch for securing a fluid delivery set in position on the pump to prevent the normal operative relationship between the set and the pump from being upset during a fluid pumping operation.

2. Discussion of the Prior Art

It is conventional to provide perenteral or enteral nutrition to certain patients who require the infusion of fluids, and to meter the delivery of such fluids to the patient by providing a peristaltic pump between a prefilled fluid container and the patient.

Typically, the delivery system includes a set comprising the container, a drip chamber, a delivery outlet, and tubing connecting these elements together. The tubing extending between the drip chamber and the delivery outlet is provided with a small coupler by which the tubing is supported relative to the pump.

The drip chamber and the coupler are secured to the pump, with the tubing between the chamber and flange being stretched around a rotor of the pump. By supporting the fluid delivery set relative to the pump in this fashion, rotation of the rotor causes fluid to be peristaltically delivered to the outlet at a rate controlled by the speed of rotation of the rotor.

Numerous problems exist with this type of conventional construction. For example, no structure is provided in conventional devices which prevents the fluid delivery set from simply being unwrapped from the supported position relative to the pump, and removed from the device. Thus, it is possible for the tubing between the drip container and the outlet to be either inadvertently or intentionally removed from engagement with the rotor such that a continuous stream of fluid is allowed to be delivered unmetered directly to the patient's stomach, possibly resulting in catastrophic over-infusion.

One attempt at overcoming this shortcoming in conventional systems calls for the use of a magnetic field detector positioned on the device adjacent the point at which the coupler is supported, and the coupler includes a magnetic element capable of being recognized by the detector. Thus, a warning signal may be generated if the coupler is removed from its proper operative position.

However, it is still possible with this known device to inadvertently remove the fluid delivery set simply by pulling on the set so that it is lifted from the device. No structure is provided in the conventional constructions to prevent such removal of the delivery set.

OBJECTS AND SUMMARY OF THE INVENTION

It is an object of the present invention to provide a medical fluid pump apparatus which permits a fluid delivery set to be secured in an operative position relative to a pump and prevents the set from being inadvertently pulled from this position, in order to reduce the possibility of catastrophic over-infusion of the fluid into a patient.

It is another object of the present invention to provide a medical fluid pump apparatus including a latch for securing the set in place, and a control means for enabling operation of the pump only when the latch is closed to prevent removal of the set from the operative position.

In accordance with these and other objects evident from the following description of a preferred embodiment, a medical fluid pump apparatus includes a peristaltic pump and a housing on which the pump is supported. The housing includes a shelf spaced from the pump and provided with a pair of spaced, transverse slots sized for receipt of the tubing of the fluid delivery set so that the tubing of the fluid delivery set may be received in the slots and placed in operative engagement with the peristaltic pump.

A latch is supported on the housing for movement between a closed position in which the latch blocks the slots to prevent the removal of the tubing from the slots and an open position in which the latch exposes the slots to permit insertion and removal of the tubing.

The latch is preferably supported for pivotal movement about a support axis and for translational movement along the axis relative to the housing so that the latch is opened by pulling axially on the latch and then turning it to the open position exposing the slots. A detection means may also be provided for detecting when the latch is in the closed position so that a suitable signal may be delivered to a central processing unit that enables operation of the pump only when the latch is closed.

Numerous advantages are realized by constructing a medical fluid pump apparatus in accordance with the present invention. For example, by providing a single latch that simultaneously blocks off two adjacent slots within which the set is received, setup of the apparatus is simplified since it is only necessary to move the one latch between the open and closed position to secure the set in place.

In addition, by providing the construction of the present invention, the set is held in place on the apparatus and may not be pulled from the operative position without first opening the latch. Thus, catastrophic unmetered flow of medical fluid into the patient is prevented.

The pull-and-turn action of the latch prevents small children from intentionally removing the set from the pump so that the apparatus may be used in pediatric applications. In addition, even if the latch is operated intentionally during a fluid pumping operation, this opening of the latch is detected, and the apparatus provides an alarm signal, deactivation of the pump, or both in response to the detection.

BRIEF DESCRIPTION OF THE DRAWING FIGURES

A preferred embodiment of the present invention is described in detail below with reference to the attached drawing figures, wherein:

FIG. 1 is a perspective view of an enteral pump apparatus constructed in accordance with the present invention, and a fluid delivery set adapted for use with the apparatus;

FIG. 3 is a fragmentary sectional view of the apparatus taken along line 3—3 of FIG. 2;

FIG. 4 is a fragmentary sectional view of the apparatus taken along line 4—4 of FIG. 2;

FIG. 5 is a fragmentary sectional view of the apparatus taken along line 5—5 of FIG. 7;

FIG. 6 is a fragmentary sectional view of the apparatus taken along line 6—6 of FIG. 8;

DETAILED DESCRIPTION OF THE PREFERRED EMBODIMENT

Figure 9:
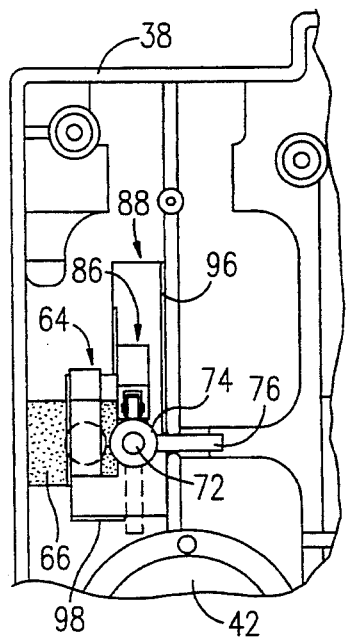
FIG. 9 is a fragmentary rear elevational view of the apparatus, with a rear panel of the housing removed.

A medical fluid supply system constructed in accordance with a preferred embodiment of the present invention is illustrated in FIG. 1, and includes a fluid delivery set 10 and a pump apparatus 12.

The fluid delivery set includes a fluid reservoir 14, a drip chamber 16, a coupler 18, shown in FIG. 3, outlet tubing 20, and tubing sections 22, 24 connecting the reservoir, drip chamber and coupler together. The reservoir 14 preferably is a flexible container constructed of a suitable food grade material, such as a Class VI food grade vinyl, and includes an outlet to which the section of tubing 22 is connected.

The section of tubing 22 connected to the container is transparent food grade PVC to allow a user to detect whether fluid is present in the tubing. The section of tubing 22 is connected to the drip chamber 16 at the top end of the chamber, and the chamber includes a diameter larger than the tubing so that when the chamber is oriented vertically, fluid traveling through the chamber drips from the upper end of the chamber to the lower end. A triangular cap 26 is provided on the chamber for holding the chamber on the pump apparatus during use. As with the other delivery set components, the drip chamber is formed of food grade materials.

The section of tubing 24 connected to the lower end of the drip chamber is also formed of precision metered silicone tubing which is opaque, but is more flexible than the tubing 22 so that the section of tubing 24 may be elongated and wrapped around a rotor 28 of the pump apparatus when the set 10 is secured to the apparatus 12.

As shown in FIG. 3, the coupler 18 is also connected to the section of tubing 24, and includes an annular flange 30 which permits the coupler to be mounted on the apparatus. The outlet tubing 20, which is formed of transparent precision metered silicone, is connected to the coupler opposite the flexible tubing 24 and extends to a conventional outlet. Although not shown, a manually operable valve may be provided on the section of tubing 22 between the reservoir and the drip chamber to permit the flow of fluid from the reservoir to be turned on and off.

Returning to FIG. 1, the pump apparatus 12 broadly includes a housing 32 on which a user interface 34 is provided, a peristaltic pump 36 supported on the housing, and mounting structure for supporting the drip chamber 16, coupler 18, and tubing 20, 24 of the delivery set relative to the pump apparatus.

The housing 32 is preferably formed of plastic or other suitable material, and includes a front panel 38 on which the user interface is provided, and a rear panel 40 that closes off the interior of the housing from exposure to the elements. The user interface includes a number of input keys for turning the device on and off and for setting various parameters for operation of the device, such as the speed of the pump and the volume of the dose to be pumped during a fluid delivery operation. The user interface also includes an output display for providing an indication of the user input and of various functions monitored by the apparatus during operation.

Figure 10:
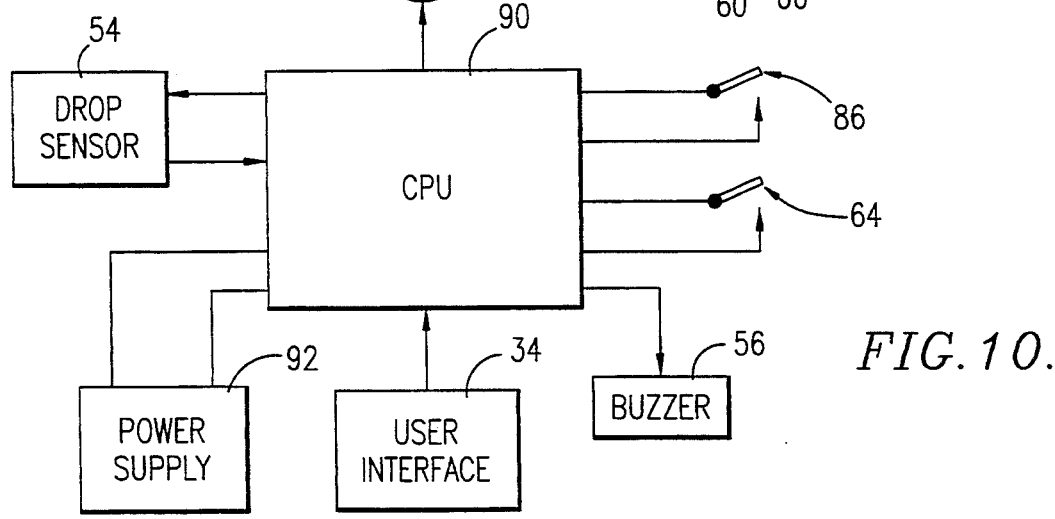
FIG. 10 is a schematic diagram of the apparatus, illustrating the control system used in the apparatus.

The peristaltic pump 36 includes the rotor 28 which is connected to the output shaft of a stepper motor 42, shown schematically in FIG. 10, and is of conventional construction. The rotor is supported on the housing a fixed distance beneath the mounting structure for the drip chamber and the coupler so that when the drip chamber and coupler are received in the mounting structure, the section of tubing 24 is stretched around the rotor allowing the rotor to peristaltically pump fluid through the tubing when rotated.

The mounting structure for supporting the drip chamber includes an upper socket 44 exposed to the front of the housing by a slot 46, and having a shape corresponding to the shape of the cap 26 on the drip chamber 16. The drip chamber is supported within the socket by positioning the chamber within the slot 46 and lowering the chamber into the socket so that the cap seats in the bottom of the socket.

A shelf 48 is defined on the front panel 38, and includes a slot 50 aligned with the upper slot 46, as shown in FIG. 4. The slot 50 includes an enlarged, crescent-shaped socket 52, shown in FIG. 7, which is sized to receive the lower end of the drip chamber so that it may not be pulled away from the housing without first lifting the chamber from the socket. The slot 50 defines a pair of side walls which are tapered inward toward the socket and which may also be slightly tapered inward from the top of the slot toward the bottom of the slot.

The pump apparatus includes a conventional two-part drop sensor 54, shown schematically in FIG. 10, located immediately below the upper socket 44 on opposite sides of the slot 46. The sensor is positioned so that when the drip chamber is held in the proper vertical position in the upper and lower sockets 44, 52, the sensor detects fluid flow as it drips from the tubing 22, and signals an alarm 56, shown in FIG. 10, if the flow varies from a predetermined rate. The drip chamber must be precisely positioned in the upper and lower sockets for the proper functioning of the sensor, or the alarm will be signalled.

The alarm 56 is conventional, such as a flashing message on the output display or an audible alarm, or both. In addition to signalling the alarm if the proper flow is not detected, the sensor 54 may also signal the motor of the pump unit to shut off, so that the pump cannot be operated until the container is properly seated in the upper socket.

The mounting structure for the coupler 18 includes a slot 58 provided in the shelf 48 and spaced laterally from the slot 50. This slot 58 also includes a crescent-shaped socket 60 defining a seat against which the flange 30 rests when the set is properly assembled on the housing. The slot 58 is slightly wider than the slot 50 and includes side walls which are tapered inward toward the socket and which may also be tapered inward from the top of the slot toward the bottom of the slot.

As shown in FIG. 1, an additional slot 62 is formed in the front panel of the housing above the shelf 48, and is sized slightly smaller than the diameter of the outlet tubing 20 so that the tubing is compressed when forced into the slot. The inner end of the slot 62 is of an increased diameter which defines a seat within which the tubing rests when pressed completely into the slot.

Turning to FIG. 3, a sensing means is provided on the housing for sensing the presence of the annular flange within the socket 60. The sensing means includes a micro-switch 64 which protrudes into the socket 60 and is movable between an open position located above the seat and a depressed, closed position, shown in FIG. 3. The micro-switch 64 is retained within a pliant elastomeric boot 66 which protects the switch from exposure to fluids but which does not inhibit movement of the switch to the closed position.

Figure 8:
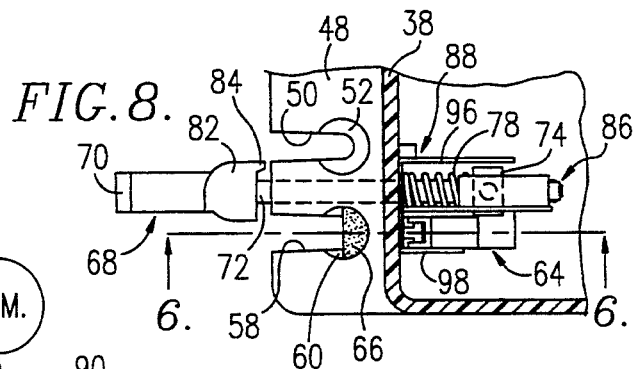
FIG. 8 is a fragmentary sectional view of the apparatus, illustrating the latch in an open position.

A latch 68 is supported on the housing for movement between a closed position, shown in FIGS. 2, 3, 4 and 9, in which the latch blocks the slots 50, 58 to prevent the removal of the section of tubing 24 and an open position, shown in FIGS. 6 and 8, in which the latch exposes the slots 50, 58 to permit insertion and removal of the tubing. The latch includes a generally U-shaped latch body 70 secured to an elongated cylindrical shaft 72 which defines a support axis of the latch. The shaft is slidably and rotatably received within an opening extending through the front panel 38, and includes an end piece 74 opposite the latch body, as shown in FIG. 4. The end piece prevents the latch from being pulled completely from the housing, and includes a radially extending finger 76. A compression spring 78 is received on the shaft 72 between the end piece and the front panel of the housing for resisting translational movement of the latch away from the closed position. By providing this construction, the latch is supported on the housing for both pivotal movement about the shaft and translational movement along the shaft relative to the housing.

The latch body 70 protrudes from the shelf when the latch is closed, and defines a pair of legs 80, 82 which extend from the body in a direction generally parallel with the shaft 72. Each leg 80, 82 is shaped and sized for receipt within one of the slots 50, 58 so that it is only possible to move the latch into the slots in one direction, and the orientation of the latch body may not be reversed.

Figure 7:
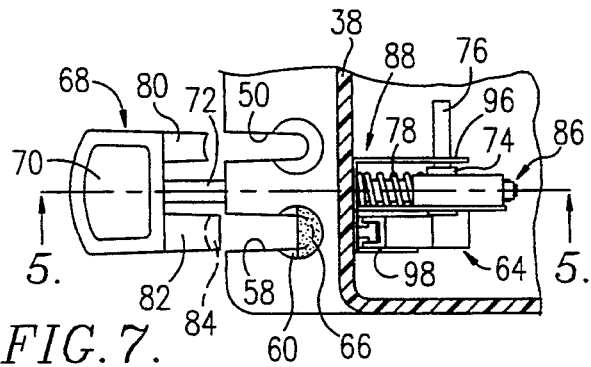
FIG. 7 is a fragmentary sectional view of the apparatus, illustrating the latch in an intermediate, extended position.

More specifically, as shown in FIG. 7, the leg 80 includes a pair of opposed side walls which are tapered inward toward the distal end of the leg, and which are tapered inward from an upper surface of the leg toward the lower surface to mate with the sides of the slot 50. The distal end of the leg 80 is curved to provide room within the socket 52 for the lower end of the drip container, as shown in FIG. 4.

The leg 82 also includes a pair of opposed side walls, as shown in FIG. 7, that are tapered inward toward the distal end of the leg, and which are tapered inward from an upper surface of the leg toward the lower surface. The distal end of the leg 82 is curved to provide room within the socket 60 for the annular flange 30, and includes a protruding lip 84, best shown in FIG. 3, along the upper surface of the leg which overlaps the flange and holds it in the socket 60 when the latch is closed.

A detection means is supported on the housing for detecting when the latch 68 is in the closed position. As illustrated in FIG. 3, the detection means preferably includes a micro-switch 86 supported on a bracket 88 from the rear surface of the front panel 38. The micro-switch extends into the path of the end piece 74 of the latch so that when the latch is closed, the end piece depresses the switch upward to a closed position. When the latch is pulled from the housing, the end piece is removed from engagement with the switch and the switch opens.

Turning to FIG. 10, the control system used to monitor the status of the micro-switches 64, 86 and the drop sensor 54 is shown. The system includes a control means 90, preferably a CPU, for allowing operation of the stepper motor 42 only when the micro-switch 86 detects the latch in the closed position and the micro-switch 64 senses the presence of the flange against the seat. When these conditions are satisfied and the switches 64, 86 are closed, power is provided from a suitable AC or DC power supply 92 to the stepper motor of the pump and the stepper motor is operated at a speed controlled by the data input at the user interface 34.

During operation of the apparatus, if the drop sensor 54 fails to detect the proper rate of flow through the drip chamber, a signal is delivered to the CPU and the alarm 56 is activated. In addition, if either of the micro-switches 64, 86 are opened, the CPU will interrupt operation of the pump, activate the alarm, or both.

During setup of the system, the latch is moved to the open position, as shown in FIG. 6, and the fluid delivery set is connected to the pump apparatus by first lowering the drip chamber into the upper socket 44 while aligning the tubing 24 with the lower slot 50 so that the drip chamber is seated in both the upper and lower sockets 46, 52 and is aligned with the two-part flow detector, which is mounted adjacent openings 94 on either side of the slot, as shown in FIG. 4.

Thereafter, as illustrated in FIG. 1, the tubing 24 is stretched around the rotor 28 and is pulled upward with sufficient force to stretch the tubing so that the tubing may be positioned in the slot 58 with the coupler 18 disposed above the shelf 48. When the tubing is released, the coupler is drawn toward the rotor with enough force to pull the annular flange 30 into the socket 60, depressing the micro-switch 64 so that a signal is received by the CPU 90 indicative of the proper seating of the flange. The outlet tubing 20 downstream of the flange 30 is then pressed through the upper slot 62 and held in place by the friction fit provided by the slot.

Once the fluid delivery set 10 is positioned on the apparatus, the latch 68 is turned 90° from the position shown in FIG. 6 to the position shown in FIG. 5, so that the legs are aligned with the slots, as shown in FIG. 7. The latch is then released, allowing the spring 78 to pull the latch from this intermediate position to the fully closed position, shown in FIG. 2.

Turning to FIG. 3, the lip 84 on the leg 82 of the latch engages the upper surface of the annular flange 30 when the latch is closed and holds the coupler in the socket 60 so that it may not be pulled upward away from the shelf 48. Thus, the coupler 18 is locked in place and may not be removed without first opening the latch. Likewise, the other leg 80 mates with the slot 50 to prevent both the tubing and the lower end of the drip chamber from being pulled from the apparatus, as shown in FIG. 4.

The combination provided by the latch 68 at the lower end of the drip chamber, the socket 44 at the upper end of the chamber, and the downward tension exerted on the chamber by the tubing 24 stretched around the rotor, secures the drip chamber 16 in the proper operative position relative to the two-part flow detector and prevents the drip chamber from pulled from the apparatus without first being lifted against the bias of the tubing by a distance sufficient to clear the upper socket.

Figure 2:
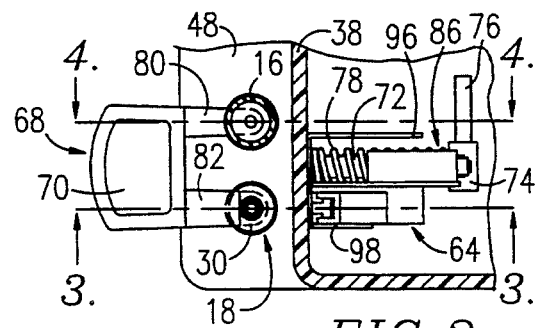
FIG. 2 is a fragmentary sectional view of the apparatus, illustrating a latch in the closed position, and a portion of the housing along which the latch is supported.

In order to change the fluid delivery set 10 upon completion of a fluid pumping operation, the latch 68 is opened by first pulling the latch axially away from the housing to the intermediate position, shown in FIG. 7, in which the legs 80, 82 clear the slots 50, 58. In the closed position of the latch, as shown in FIG. 2, the side walls of the legs 80, 82 mate with the side walls of the slots 50, 58 to prevent the latch from being pivoted relative to the shelf. Therefore, the latch may not be pivoted unless it is first moved axially to the intermediate position. By providing this construction, two separate coordinated movements are required to open the latch, rendering inadvertent opening of the latch impossible.

As shown in FIG. 9, the bracket 88 includes a pair of lugs 96, 98 which extend rearward of the front panel into the path of movement of the finger on the end piece of the support shaft when the latch is turned to either end of the desired range of motion of the latch. Thus, it is only possible to turn the latch back and forth within a 90° range of motion extending between the closed position and the open position.

As shown in FIG. 5, if the latch is pulled from the closed position during a fluid pumping operation, the micro-switch 86 is opened, signalling the CPU to both alert the user that the latch is not properly closed, and to shut off power to the stepper motor so that further pumping is interrupted. A similar result is produced if the coupler 18 is pulled from beneath the lip 84 of the latch away from the micro-switch 64.

Although the invention has been described with reference to the preferred embodiment illustrated in the attached drawing figures, it is noted that substitutions may be made and equivalents employed herein without departing from the scope of the invention as recited in the claims.

What is claimed is:

1. A medical fluid pump apparatus for use with a fluid delivery set including a fluid reservoir, a delivery outlet, and tubing connecting the reservoir to the outlet, the apparatus comprising:
   a pump;
   a housing on which the pump is supported, the housing including a shelf spaced from the pump and provided with a pair of spaced, transverse slots sized for receipt of the tubing of the fluid delivery set so that the tubing of the fluid delivery set may be received in the slots and placed in operative engagement with the pump;
   a latch supported on the housing for movement between a closed position in which the latch blocks the slots to prevent the removal of the tubing from the slots and an open position in which the latch exposes the slots to permit insertion and removal of the tubing,
   the latch being generally U-shaped, including a pair of legs spaced from one another by a distance equal to the spacing between the slots, each leg being sized for receipt within one of the slots so that when the latch is in the closed position the legs extend into and block the slots,
   wherein the latch is supported on the housing for pivotal movement about a support axis and for translational movement along the support axis relative to the housing; and
   a catch means for preventing the latch from being pivoted about the support axis when the legs are positioned at least partially within the slots and for allowing the latch to be pivoted after the latch has been translated along the support axis by a distance sufficient to remove the legs from the slots.

2. A medical fluid pump apparatus as recited in claim 1, wherein one of the slots is formed of a width different from the width of the other slot, and the legs are formed of widths corresponding to the widths of the slots so that the legs engage the slots when the latch is in the closed position to prevent the latch from being pivoted about the support axis.

3. A medical fluid pump apparatus as recited in claim 1, further comprising biasing means for resisting translational movement of the latch away from the closed position.

4. A medical fluid pump apparatus as recited in claim 1, further comprising a limit means for limiting the range of pivotal movement of the latch relative to the housing.

5. A medical fluid pump apparatus for use with a fluid delivery set including a fluid reservoir, a delivery outlet, and tubing connecting the reservoir to the outlet, the apparatus comprising:
   a pump;
   a housing on which the pump is supported, the housing including a shelf spaced from the pump and provided with a pair of spaced, transverse slots sized for receipt of the tubing of the fluid delivery set so that the tubing of the fluid delivery set may be received in the slots and placed in operative engagement with the pump; and
   a latch supported on the housing for movement between a closed position in which the latch blocks the slots to prevent the removal of the tubing from the slots and an open position in which the latch exposes the slots to permit insertion and removal of the tubing,
   the latch being generally U-shaped, including a pair of legs spaced from one another by a distance equal to the spacing between the slots, each leg being sized for receipt within one of the slots so that when the latch is in the closed position the legs extend into and block the slots,
   wherein the tubing with which the apparatus is used includes a drip chamber and an annular flange spaced from the drip chamber along the tubing, the slots in the holding being adapted to receive the tubing that extends between the drip chamber and the annular flange, one of the slots including a crescent-shaped seat formed in the shelf opposite the pump and on which the annular flange is received when the fluid delivery set is properly positioned on the apparatus, the leg of the latch sized for receipt in the one slot including a lip that, when the latch is in the closed position, extends into the slot by a distance sufficient to engage the annular flange positioned on the seat and prevent the flange from being lifted from the seat.

6. A medical fluid pump apparatus as recited in claim 5, further comprising a detection means for detecting when the latch is in the closed position.

7. A medical fluid pump apparatus as recited in claim 6, further comprising a sensing means for sensing the presence of the annular flange against the seat.

8. A medical fluid pump apparatus as recited in claim 7, further comprising control means for allowing operation of the pump only when the detection means detects the latch in the closed position and the sensing means senses the flange against the seat.

9. A medical fluid pump apparatus as recited in claim 8, further comprising a drop sensing means aligned with the drip chamber when the fluid delivery set is properly positioned on the apparatus for sensing fluid flow into the drip chamber during operation of the apparatus, the control means allowing operation of the pump only when the sensed fluid flow is within a predetermined range of flow rates.

10. A medical fluid pump apparatus for use with a fluid delivery set including a fluid reservoir, a delivery outlet, and tubing connecting the reservoir to the outlet, the apparatus comprising:
   a pump;
   a housing on which the pump is supported, the housing including a shelf spaced from the pump and provided with a transverse slot sized for receipt of the tubing of the fluid delivery set;
   a latch supported on the housing for movement between a closed position in which the latch blocks the slot to prevent removal of the tubing from the slot and an open position in which the latch exposes the slot to permit insertion and removal of the tubing; and
   a detection means for detecting when the latch is in the closed position,
   wherein the latch includes a leg sized for receipt within the slot so that when the latch is in the closed position, the leg extends into and blocks the slot, the latch being supported on the housing for pivotal movement about a support axis and for translational movement along the support axis relative to the housing.

11. A medical fluid pump apparatus as recited in claim 10, the apparatus further comprising a catch means for preventing the latch from being pivoted about the support axis when the leg is positioned at least partially within the slot and for allowing the latch to be pivoted after the latch has been translated along the support axis by a distance sufficient to remove the leg from the slot.

12. A medical fluid pump apparatus as recited in claim 10, the tubing with which the apparatus is used including a drip chamber and an annular flange spaced from the drip chamber along the tubing, wherein the slot is adapted to receive the tubing that extends between the drip chamber and the annular flange and includes a crescent-shaped seat formed in the shelf opposite the pump and on which the annular flange is received when the fluid delivery set is properly positioned on the apparatus, the leg of the latch including a lip that, when the latch is in the closed position, extends into the slot by a distance sufficient to engage the annular flange positioned on the seat and prevent the flange from being lifted from the seat.

13. A medical fluid pump apparatus as recited in claim 12, further comprising a sensing means for sensing the presence of the annular flange against the seat.

14. A medical fluid pump apparatus as recited in claim 13, further comprising control means for allowing operation of the pump only when the detection means detects the latch in the closed position and the sensing means senses the flange against the seat.

15. A medical fluid pump apparatus as recited in claim 14, further comprising a drop sensing means aligned with the drip chamber when the fluid delivery set is properly positioned on the apparatus for sensing fluid flow into the drip chamber during operation of the apparatus, the control means allowing operation of the pump only when the sensed fluid flow is within a predetermined range of flow rates.

16. A medical fluid pump apparatus as recited in claim 10, further comprising biasing means for resisting translational movement of the latch away from the closed position.

17. A medical fluid pump apparatus as recited in claim 10, further comprising a limit means for limiting the range of pivotal movement of the latch relative to the housing.

18. A medical fluid pump apparatus for use with a fluid delivery set including a fluid reservoir, a delivery outlet, and tubing connecting the reservoir to the outlet, the tubing including a drip chamber and an annular flange spaced from the drip chamber along the tubing, the apparatus comprising:
   a pump;
   a housing on which the pump is supported, the housing including a shelf spaced from the pump and a transverse slot formed in the shelf and sized for receipt of the tubing of the fluid delivery set, the slot including a crescent-shaped seat formed in the shelf opposite the pump and on which the annular flange is received when the fluid delivery set is properly positioned on the apparatus;
   a latch including a leg sized for receipt within the slot, the latch being supported on the housing for movement between a closed position in which the leg extends into and blocks the slot to prevent removal of the tubing from the slot and an open position in which the latch exposes the slot to permit insertion and removal of the tubing,
   the leg including a protruding lip which overlaps the flange and holds it against the seat when the fluid delivery set is properly positioned and the latch is closed;
   a detection means for detecting when the latch is in the closed position;
   a sensing means for sensing the presence of the annular flange against the seat; and
   a control means for allowing operation of the pump only when the detection means detects the latch in the closed position and the sensing means senses the flange against the seat.

* * * * *